US006289715B1

(12) United States Patent
Gilbert et al.

(10) Patent No.: US 6,289,715 B1
(45) Date of Patent: Sep. 18, 2001

(54) SYSTEM FOR ANALYZING THE ATMOSPHERE IN AN ENCLOSURE FOR SOLDERING OR TINNING BY MEANS OF A METAL ALLOY

(75) Inventors: Chevalier Gilbert, Voisins le Bretonneux; Leturmy Marc, Gressey, both of (FR)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 09/603,879

(22) Filed: Jun. 26, 2000

(30) Foreign Application Priority Data

Jun. 24, 1999 (FR) .................................................. 99 08087

(51) Int. Cl.⁷ .......................... G01D 18/00; B01D 53/22; B23K 35/38; G05D 11/13
(52) U.S. Cl. .................... 73/19.01; 73/31.02; 73/863.23; 73/863.12; 95/18; 95/54
(58) Field of Search ................................ 73/19.01, 23.31, 73/31.02, 31.03, 863.23, 863.11, 863.12, 864.83; 95/273, 18, 54; 96/56.5, 56.3; 219/121.23, 129

(56) References Cited

U.S. PATENT DOCUMENTS

| | | | |
|---|---|---|---|
| 2,370,817 | * | 3/1945 | Shanley ...................................... 73/23 |
| 2,847,368 | * | 8/1958 | Worthington et al. .................. 202/46 |
| 3,186,232 | * | 6/1965 | Yates et al. .......................... 73/421.5 |
| 3,489,523 | * | 1/1970 | Clardy et al. ........................... 23/232 |
| 3,929,003 | * | 12/1975 | Lewellyn ............................. 73/61 R |
| 4,161,883 | | 7/1979 | Laird et al. ....................... 73/421.5 A |
| 4,348,886 | * | 9/1982 | Faith, Jr. .................................. 73/19 |
| 4,699,886 | | 10/1987 | Lelong ................................... 436/60 |
| 4,924,860 | | 5/1990 | Larsen et al. .................... 128/205.12 |
| 5,214,952 | * | 6/1993 | Leggett et al. .......................... 73/1 G |
| 5,376,163 | | 12/1994 | Carlson et al. ......................... 95/22 |
| 5,429,662 | * | 7/1995 | Fillet ..................................... 95/14 |
| 5,499,531 | * | 3/1996 | Henderson .......................... 73/64.45 |
| 5,665,902 | * | 9/1997 | Wang et al. ........................ 73/28.01 |
| 5,887,610 | | 3/1999 | Verbockhaven .......................... 137/3 |
| 5,918,793 | * | 7/1999 | Kopke, Sr. .......................... 228/103 |
| 6,125,687 | * | 10/2000 | McClelland et al. ............... 73/19.01 |

FOREIGN PATENT DOCUMENTS 198 50 082   5/2000 (DE).
2 779 824   12/1999 (FR).

* cited by examiner

Primary Examiner—Hezron Williams
Assistant Examiner—David J. Wiggins
(74) Attorney, Agent, or Firm—Burns, Doane, Swecker & Mathis, L.L.P.

(57) ABSTRACT

A system for analyzing a content of at least one element of a contained atmosphere for soldering or tinning with a metal alloy, comprising:

at least one sampling line for taking a gas sample from the contained atmosphere;

at least one analyzer for analyzing the element;

at least one coalescence filter located on the sampling line upstream of the analyzer;

wherein the sampling line comprises a portion, located between the contained atmosphere and the coalescence filter, wherein the formation of cold spots which could cause precipitation of solid or pasty compounds in the line portion is prevented;

a detector of a blockage in the sampling line between the enclosure and the analyzer.

11 Claims, 1 Drawing Sheet

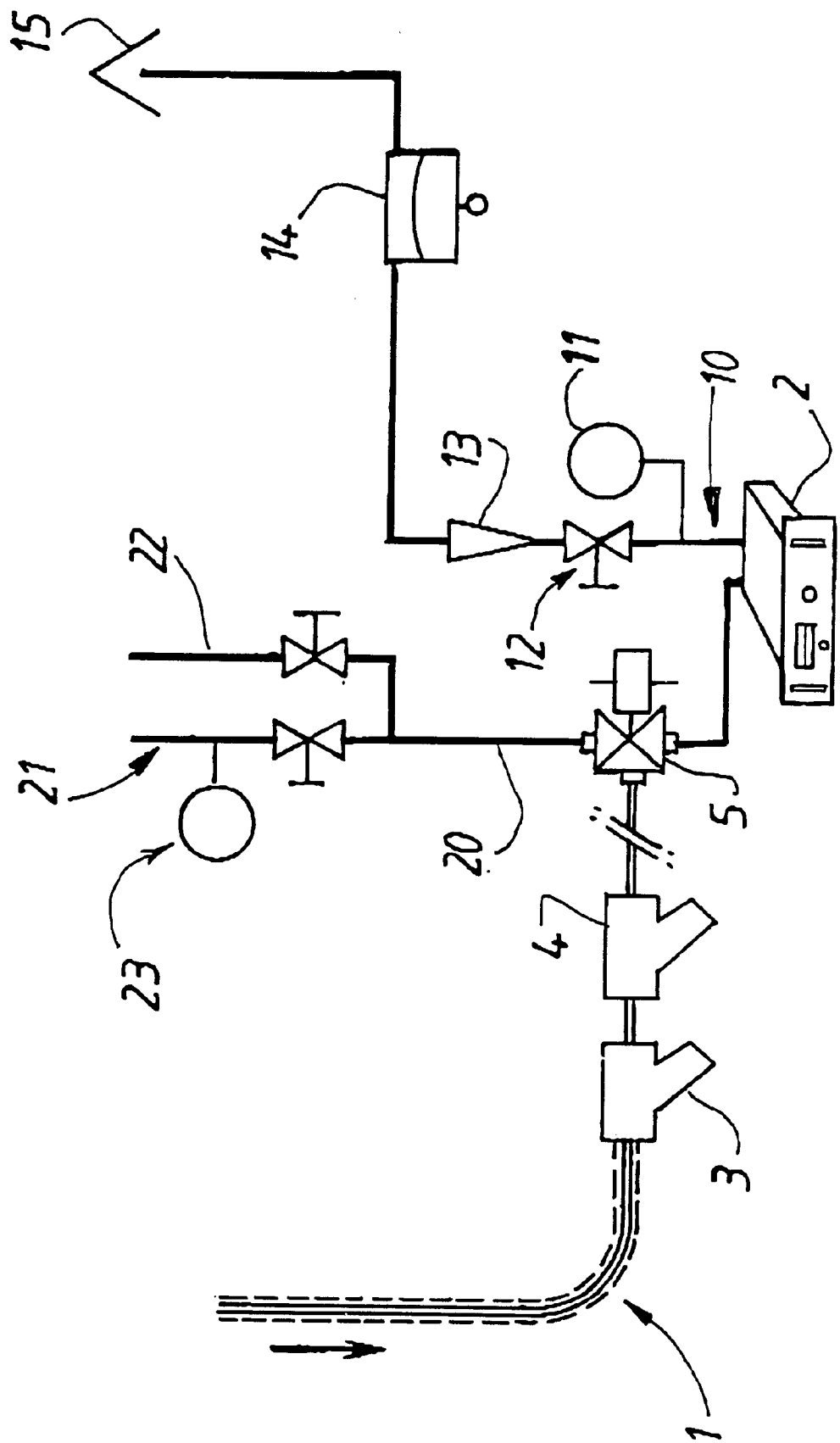

SYSTEM FOR ANALYZING THE ATMOSPHERE IN AN ENCLOSURE FOR SOLDERING OR TINNING BY MEANS OF A METAL ALLOY

BACKGROUND OF THE INVENTION (I) Field of the Invention

The present invention relates to the field of gas analysis systems and pertains more particularly to systems for analyzing the content of at least one element of the atmosphere in an enclosure used for soldering or tinning by means of a metal alloy, these soldering or tinning operations using the assistance of a chemical flux which conventionally comprises one or more components among acids, alcohols, or resins, especially rosins.

(II) Description of the Related Art

Soldering and tinning operations are carried in particular in electronics. Examples include soldering of electronic components on a circuit, soldering of circuits in module backplanes, or else termination tinning of electronic components.

The role of the fluxing is then to clean the metal surfaces to be soldered or tinned (degreasing, deoxidation, decontamination of absorbed layers, etc.), the purpose of this being to facilitate the subsequent wetting of these surfaces by the solder.

This fluxing operation is therefore, most commonly, carried out by means of chemical fluxes, often obtained from a resinous base to which, in particular, acid components are added.

It will therefore be noted that two of the most commonly used methods for carrying out such soldering operations in electronics are called "wave soldering" and "reflow soldering."

In the first case of wave-soldering machines, the design of these machines is such that the parts to be soldered or tinned are brought into contact with one or more liquid solder waves obtained by making the solder bath contained in a tank flow through a nozzle. The parts (circuit, component) have generally been fluxed beforehand in a zone upstream of the machine, by means of a flux spray or foam, the fluxing operation being followed by a preheating operation which is done to activate the fluxes deposited beforehand on the circuit and to preheat the circuits or components before their arrival in the hot soldering zone.

In the case of the second type of method, called reflow soldering, which moreover combines several techniques under this name, it is not a bath of liquid solder that is used but a solder paste containing the solder alloy, in which paste formulation the chemical flux is included, which paste is deposited on the substrate and to which paste a certain amount of heat allowing the metal alloy to melt is supplied; usually, this heat transfer is carried out in a continuous oven.

It is becoming increasingly commonplace for industrial gas users (electronics, heat treatment, food, etc.) to be required to analyze one or more components of the atmosphere that they employ at a given user station, so as to be in a position to carry out a complete quality control of the parts treated, complete quality control assuming, in particular, that it is possible to know under which atmosphere conditions each part has been treated.

Depending on the intended application, safety conditions (risks of explosion) also apply.

Gas consumers therefore usually want to be able to know these atmosphere conditions, or indeed to display them, to archive them, to have traceability and even to process these values thus archived.

It is therefore considered necessary to be able to be in a position to offer industrial gas consumers analytical methods and equipment allowing gas samples to be taken at the various analysis points monitored in the enclosure used for the treatment, making it possible to minimize the response time of the analyzer or analyzers in question and to ensure that the analytical bay is provided with gas samples which are representative of the atmosphere in the enclosure.

By way of illustration, reference may be made to the following documents in the name of the Applicant, which also relate to this field of atmosphere analysis or of atmosphere regulation in soldering or tinning enclosures: FR 98-07498 or EP-A839,599.

The work that Applicant has conducted in this field has raised questions about the reliability of the analytical systems currently present in such soldering or tinning plants, and especially the information in terms of residual oxygen content of the atmosphere in the enclosure for operations carried out under nitrogen.

These uncertainties raise serious doubts regarding the production quality from the soldering or tinning machines in question.

SUMMARY AND OBJECTS OF THE INVENTION

One of the objectives of the present invention is therefore to provide a solution to the above-mentioned technical problems, and therefore especially to improve the reliability of gas analysis systems operating on such processes for soldering or tinning by means of a metal alloy and in the presence of chemical fluxes.

The system according to the invention for analyzing the content of at least one element of the atmosphere in an enclosure for soldering or tinning by means of a metal alloy, comprises the following elements:

- at least one sampling line for taking a gas sample from the enclosure;
- at least on analyzer capable of analyzing the element;
- at least one coalescence filter located on the sampling line upstream of the analyzer;
- a means for allowing that portion of the sampling line which is located between the enclosure and the coalescence filter to be devoid of cold spots which could cause precipitation of solid or pasty compounds in the line portion;
- a means for detecting any blockage in the sampling line between the enclosure and the analyzer.

Moreover, the system according to the invention optionally comprises one or more of the following characteristics:

- several coalescence filters of different grades, placed in series on the sampling line upstream of the analyzer;
- at least two coalescence filters placed in series, offering increasing retention performance along the gas sampling path;
- the at least one coalescence filter is positioned in the immediate vicinity of the wall of the enclosure where the sampling line is connected;
- the at least one coalescence filter is positioned near the wall of the enclosure where the sampling line is connected and the sampling line portion going from the wall to the coalescence filter has been thermally insulated;

the system includes a heater for the sampling line portion located between the enclosure and the coalescence filter, which is capable of heating this line portion to a temperature above the temperature below which precipitation phenomena in compounds (i.e., solid, semisolid, liquid or pasty compounds) may occur;

the system includes a pressure controller located downstream of the analyzer, on its gas removal line, and upstream of a pumping device;

the system includes a pressure controller or a flow meter located upstream of the analyzer;

the system includes a device for cooling the at least one coalescence filter, such as a fan.

One of the merits of the present invention is that it can demonstrate the lack of reliability of the current atmosphere analysis systems in such plants for soldering or tinning with a metal alloy, especially those concerned with analyzing the residual oxygen content in nitrogen-based soldering or tinning atmospheres. This lack of reliability is specially associated with the sampling methods in these analysis systems.

The Applicant has especially been able to demonstrate that the analytical results provide, for example, an extremely low residual oxygen content in the nitrogen-based atmosphere, leaving the operator to believe that his soldering process is perfectly inerted, but not reflecting the actual residual oxygen content conditions in his soldering enclosure.

In fact, it should be emphasized that the chemical soldering or tinning fluxes normally used in these operations are resin-based formulations, especially rosins, in which there is also, in particular, the presence of alcohol and of acid.

In this context, the following comments may therefore be made:

a) because of the presence of alcohol in the atmosphere analyzed, a measurement technology which uses a zirconium oxide probe proves difficult to employ since the high temperature of the measurement cell causes oxidation by the residual oxygen in the atmosphere of the hydrocarbons present, the measurement is therefore falsified by the disappearance of the oxygen b) however, the presence of reducing species in the atmosphere is not, moreover without entailing risks of the oxide of the cell being reduced;

c) so-called low-content electrochemical cells are often used for their resistance to hydrocarbons, which cells Save, however, the drawback of not withstanding high oxygen contents for a long time.

This is because they become saturated with oxygen and do not return very easily to low contents oxygen, the time taken to return to low contents being: of course, an increasing function of the time for which the cell was exposed to oxygen.

It should also be stressed that these cells are electrochemical cells which are consumed, their longevity being directly proportional to the amount of oxygen that they will have seen flow, and therefore typically a client's production stoppage meaning that inerting is no longer ensured- there is a risk of the associated analyzers being exposed for a certain time to air; and oxygen d) the composition of the fluxes used may give rise to the precipitation in the lines of residues—solid, semisolid, liquid or pasty residues—such as cured rosins, and therefore to the fact that the sampling circuit may be partially or even completely obstructed. It is possible in this case to observe, paradoxically, extremely low residual oxygen measurements being obtained, leaving the operator to believe, falsely, that his soldering process is perfectly inerted.

This is because, when a blockage is present, the pump of the analyzer draws a vacuum in the remaining portion, therefore resulting in very low residual oxygen measurements via a first mechanism.

Moreover, the electrochemical cell will consume the little residual oxygen which remains in the free line portion, therefore also resulting in very low residual oxygen measurements via this second mechanism.

e) gas sampling may also result in solid particles such as soldering tin dust.

As will have been understood on reading the foregoing, the combination of characteristics of the analytical system according to the invention provides an extremely advantageous solution to the drawbacks encountered in the current analytical methods.

The plant makes it possible, in particular, to convey the sampled gas right to the filtration unit under conditions which prevent the deposition of residues, but also effectively to stop the undesirable contaminants (especially, the aerosol forms) before they contaminate the analyzers.

The system also makes it possible to obtain the longevity of the cells and to effectively detect any onset of a sampling circuit becoming blocked, which could degrade the reliability of the analytical measurements delivered.

Further characteristics and advantages will emerge from the following description given solely by way of example and with reference to the appended drawing.

BRIEF DESCRIPTION THE DRAWING

The FIGURE is a schematic representation of an analytical system according to the invention.

DETAILED DESCRIPTION OF PREFERRED EMBODIMENTS

The present application claims the benefit under 35 U.S.C. §119 of French patent application 99 08087, the disclosure of which is hereby incorporated by reference.

The FIGURE provides an example of an atmosphere analysis system according to the invention, allowing the residual oxygen content in a nitrogen-based atmosphere used in a reflow soldering oven or a wave soldering machine in electronics to be analyzed.

In the FIGURE, an oxygen analyzer 2 is shown. In this case, the analyzer is one of the electrochemical cell type.

A sample of the gas to be analyzed reaches the analyzer 2 via the sampling line 1, passing successively through two coalescence filters 3 and 4, of different specification.

Coalescence filters are usually referred to in terms of "percentage of particles stopped having a diameter greater than a given value:" for example, a filter will be referred to as one stopping 99% of particles greater than 0.6 $\mu$m.

In the FIGURE, the filters 3 and 4 have increasing retentabilities: for example, the first filter 3 is designed to stop 95% of particles greater than 0.3 $\mu$m while the filter 4 is designed to stop 99.9% of the remaining particles.

For the embodiment shown, that portion of the sampling line 1 which is located between the enclosure (not shown in the figure) and the first coalescence filter 3 is equipped here with a trace heating cable (shown in the figure by a doffed line) allowing the sampling line portion in question to be heated to a temperature high enough to prevent liquid or solid deposits in the one (for example about 150° C. and higher).

The gas sample thus filtered then flows to a three-way solenoid valve 5 and from there to the analyzer 2.

Downstream of the analyzer, there is a gas removal line 10 leading, by passing is through a diaphragm pump 14, to a vent 15. It should be noted in this removal line 10 that there is a control valve 12 and a flow meter 13, but above all a blockage detection means 11 which is located immediately downstream of the analyzer and which consists here of a pressure controller set to approximately 900 mbar absolute (−100 mbar relative).

An inert gas such as nitrogen is conveyed to the analyzer 2 via the gas line 21/20, flowing through a pressure controller 23 which serves here for detecting the presence of nitrogen in the line (typically here set to 2 bar).

The line 22 optionally serves to supply the analyzer with a standard gas.

The system also includes means (not shown in the figure) allowing data acquisition and processing as well as feedback control on certain components of the system (for this purpose, it will be possible to use a programmable automatic controller, or a PC, or even hard-wired logic), so as to provide one or more of the following advantageous functions:

- acquisition and storage, continuously or at a desired interval, of the residual oxygen content measured by the analyzer 2;
- of stopping the analysis as soon as the residual oxygen content is greater than a given limit, for example 1000 ppm,
- of flushing the analyzer with the inert gas coming from the line 21, during periods of production setting or periods during which the analysis is stopped for safety reasons;
- of detecting the absence of nitrogen in the line 21 (pressure controller 23) and of warning any operators on the site of this absence with a warning signal;
- of providing an alarm (visual or audible) should nitrogen be absent or a line be blocked, or when the residual oxygen level detected by the analyzer exceeds a predetermined level (for example, 300 ppm);
- of displaying for the user the working conditions on a display screen;
- of attempting at regular intervals over time to automatically restart the analysis system so as to avoid the user having to reset the analytical cycle manually (for example as soon as the residual oxygen content has come back down below 1000 ppm);
- of definitively stopping the analytical cycle when, after several vain attempts at automatic restarting, the required condition has not been able to be fulfilled (sufficiently low residual oxygen content or else sufficient presence of nitrogen in the line 21).

It is therefore considered that the system described above provides a significant improvement to existing analytical systems, by improving the reliability and the longevity, by the combined use of one or more coalescence filters, of a sampling line portion preventing precipitation cold sports and detecting a blockage in the line.

What is claimed is:

1. A system for analyzing a content of at least one element of a contained atmosphere for soldering or tinning with a metal alloy, comprising:
    at least one sampling line for taking a gas sample from the contained atmosphere;
    at least one analyzer downstream from said contained atmosphere for analyzing said element in said gas sample;
    at least one coalescence filter located on the sampling line upstream of the analyzer;
    wherein said sampling line comprises a portion, located between the contained atmosphere and the coalescence filter, wherein the formation of cold spots which could cause precipitation of solid or pasty compounds in the sampling line portion is of prevented;
    a detector of a blockage in the sampling line between the contained atmosphere and the analyzer.

2. The system according to claim 1, wherein said contained atmosphere is in an enclosure including a wall.

3. The system according to claim 1, further comprising a plurality of coalescence filters placed in series on the sampling line, said filters having different retentabilities.

4. The system according to claim 3, wherein said plurality of coalescence filters placed in series offers increasing retentabilities along the gas sampling line.

5. The system according to claim 2, wherein said at least one coalescence filter is in an immediate vicinity of the wall of the enclosure where the sampling line is connected, so as to prevent formation of cold spots which could cause precipitation of solid or pasty compounds in the line portion.

6. The system according to claim 2, wherein said at least one coalescence filter is near the wall of the enclosure where the sampling line is connected and said portion of said sampling line, located between the wall of the enclosure and said at least one coalescence filter, is thermally insulated, so as to prevent formation of cold spots which could cause precipitation of solid or pasty compounds in the line portion.

7. The system according to claim 2, further comprising a heater for said portion of said sampling line located between the enclosure and said at least one coalescence filter, said heater being capable of heating said portion to a temperature above that in which precipitation may occur.

8. The system according claim 1, wherein said blockage detector comprises a pressure controller located downstream of the analyzer, on line, upstream of a pumping device.

9. The system according to claim 1, wherein said blockage detector comprises a pressure controller or a flow meter located upstream of the analyzer.

10. The system according to claim 1, further comprising a device for cooling said at least one coalescence filter.

11. The system according to claim 1, wherein said device is a fan.

* * * * *